US009717309B2

(12) United States Patent
Marche et al.

(10) Patent No.: US 9,717,309 B2
(45) Date of Patent: Aug. 1, 2017

(54) HOOK FASTENER

(75) Inventors: Thierry Marche, La Chapelle Basse Mer (FR); Olivier Blanc, Saint Mars du Desert (FR); Nayda Liz Ramos Medina, Cincinnati, OH (US); Michael Timothy Looney, Blue Ash, OH (US); Thomas Alexander Horn, Hofheim (DE)

(73) Assignee: APLIX, S.A., Paris (FR)

( * ) Notice: Subject to any disclaimer, the term of this patent is extended or adjusted under 35 U.S.C. 154(b) by 138 days.

(21) Appl. No.: 14/357,304

(22) PCT Filed: Nov. 10, 2011

(86) PCT No.: PCT/IB2011/002822
§ 371 (c)(1),
(2), (4) Date: Nov. 25, 2014

(87) PCT Pub. No.: WO2013/068779
PCT Pub. Date: May 16, 2013

(65) Prior Publication Data
US 2015/0074956 A1    Mar. 19, 2015

(51) Int. Cl.
*A44B 18/00* (2006.01)
*A61F 13/62* (2006.01)

(52) U.S. Cl.
CPC ...... *A44B 18/0019* (2013.01); *A44B 18/0065* (2013.01); *A61F 13/62* (2013.01); *A61F 13/625* (2013.01); *Y10T 24/27* (2015.01)

(58) Field of Classification Search
CPC . A44B 18/0019; A44B 18/0065; A61F 13/62; A61F 13/625; Y10T 24/27

USPC .......................................................... 24/452
See application file for complete search history.

(56) References Cited

U.S. PATENT DOCUMENTS

| 3,196,490 | A |   | 7/1965  | Erb |
|-----------|---|---|---------|-----|
| 4,056,593 | A |   | 11/1977 | De Navas Albareda |
| 4,775,310 | A |   | 10/1988 | Fischer |
| 4,894,060 | A |   | 1/1990  | Nestegard |
| 5,392,498 | A | * | 2/1995  | Goulait .............. A44B 18/0049 24/446 |

(Continued)

FOREIGN PATENT DOCUMENTS

| JP | 2005514976 A | 5/2005 |
| WO | WO 92/15262 | 9/1992 |

OTHER PUBLICATIONS

International Search Report for corresponding International Application No. PCT/IB2011/002822 mailed on Feb. 6, 2012 (3 pages).

(Continued)

*Primary Examiner* — Robert J Sandy
*Assistant Examiner* — Louis Mercado
(74) *Attorney, Agent, or Firm* — Bookoff McAndrews, PLLC

(57) ABSTRACT

A hook fastener including a base strip and a field of hooks, each hook having a stem and a cap, the cap including at least one lateral overhang, and each hook being further delimited by two opposing substantially planar surfaces, wherein the overhang includes a swelling located at a distance from the stem so that the thickness of the overhang increases in the swelling, the bottom surface of the overhang forming a cavity for receiving filaments.

17 Claims, 6 Drawing Sheets

(56) References Cited

U.S. PATENT DOCUMENTS

| | | | | |
|---|---|---|---|---|
| 6,080,347 | A * | 6/2000 | Goulait | A44B 18/0049 156/244.22 |
| 6,588,073 | B1 * | 7/2003 | Zoromski | A44B 18/0015 24/446 |
| 6,770,065 | B1 * | 8/2004 | Sasaki | A44B 18/0011 24/442 |
| 2003/0045856 | A1 * | 3/2003 | Couture | A44B 18/0065 604/391 |
| 2003/0120251 | A1 * | 6/2003 | Couture | A44B 18/0065 604/391 |
| 2003/0134083 | A1 * | 7/2003 | Wang | A44B 18/0003 428/99 |
| 2003/0135964 | A1 | 7/2003 | Provost et al. | |
| 2003/0145440 | A1 | 8/2003 | Ausen et al. | |
| 2003/0182776 | A1 * | 10/2003 | Ausen | A44B 18/0065 24/452 |
| 2004/0068848 | A1 | 4/2004 | Ausen et al. | |
| 2005/0081346 | A1 | 4/2005 | Clarner | |
| 2005/0132544 | A1 * | 6/2005 | Seth | A44B 18/0061 24/452 |
| 2006/0048347 | A1 | 3/2006 | Kurtz et al. | |
| 2014/0000003 | A1 * | 1/2014 | Ashraf | A61F 13/514 2/69 |

OTHER PUBLICATIONS

Jun. 23, 2015, Translation of JP Office Action issued in JP App. No. 2014-540564.

\* cited by examiner

HOOK FASTENER

CROSS-REFERENCE TO RELATED APPLICATIONS

This application is a National Stage filing under 35 U.S.C. §371 of International Application No. PCT/IB2011/002822, filed Nov. 10, 2011, the entirety of which is incorporated by reference herein.

FIELD OF THE INVENTION

The present invention relates generally to hook fasteners, and particularly to hook fasteners adapted to be attached to a counterpart comprising retaining filaments, by the cooperation of the hooks with said filaments.

BACKGROUND OF THE INVENTION

Mechanical fasteners comprising a female fastening element with retaining filaments and a male fastening element (hook fastener) with hooks for releasably engaging the filaments are commonly used, notably on hygiene products, for example disposable wearable articles, and especially disposable wearable absorbent articles such as diapers.

Because they are economical, provide high softness, and allow keeping continuity with the remaining disposable garment which, usually, is made itself of nonwoven material, nonwoven materials have progressively replaced woven or knitted loop fastener materials for the female fastening element of such mechanical fasteners, especially in the hygiene field.

However, commercially available hook fasteners commonly used with woven or knitted loop fastener materials have proved to be inappropriate for nonwoven materials.

Some of the known hook fasteners provide little engagement with the female counterpart of nonwoven material, because their hooks have large-sized heads unable to properly penetrate the mass of interlaced filaments. Such hook fasteners lead with use to inopportune opening of the mechanical fastener, also known as "pop off".

Other hook fasteners provide sufficient engagement, but the strength which has to be applied by the customer for opening the mechanical fastener is too high, leading to a breaking of the filaments, also known as "fuzzing". Fuzzing has a negative visual impact and may well make the mechanical fastener unusable after repetitive closing and reopening thereof.

Attempts to provide new types of hook fasteners allowing better cooperation notably with nonwoven materials have been made in U.S. Pat. No. 4,894,060 and US Patent Publication No. 2004/0068848.

U.S. Pat. No. 4,894,060 discloses a hook fastener having hooks with small dimensions, allowing easy penetration into the counterpart. However, the hooks do not allow a good retention of the filaments and individually have little holding power.

US Patent Pub No. 2004/0068848 discloses a process for producing hook fasteners having hook heads with little thickness in transverse direction, adapted to cooperate with nonwoven materials. These fasteners, however, do not easily engage with the retaining filaments of the counterpart and cannot be safely removed from their counterpart without breaking the retaining filaments.

In view of the foregoing, there is still a need for providing an improved hook fastener engageable with a female counterpart having filaments, particularly a nonwoven counterpart.

SUMMARY OF THE INVENTION

One object of the present invention is to provide a hook fastener allowing a better penetration of the hooks into the counterpart material, a better capturing and retaining of the filaments after penetration, and a safe removal from the counterpart, without breaking the filaments.

According to one aspect of the present invention, there is provided a hook fastener, adapted to be attached to a counterpart comprising retaining filaments by the cooperation of its hooks with said filaments, including a base strip, and a field of hooks comprising gripping hooks protruding from said strip, each gripping hook comprising a stem which extends in its main direction and is topped by a cap, said cap including at least one overhang extending laterally from said stem, and each gripping hook being further delimited, at least at its cap portion, in its transverse direction, by two opposing substantially planar surfaces, wherein the overhang comprises a swelling located at a distance from the stem so that the thickness of the overhang increases in said swelling from an intermediate region of the overhang located between said swelling and said stem in a direction towards the bottom surface of the overhang forming a cavity for receiving the filaments of the counterpart in the vicinity of said intermediate region, and characterized in that the cavity width measured in the lateral direction of the hook, between the low point of the bottom surface of the overhang and the facing part of the gripping hook, is equal to at least 2 times a predetermined distance, the cavity depth measured in the main direction of the gripping hook, between the low point of the bottom surface of the overhang and the high point of said surface, is equal to or greater than 0.4 times the predetermined distance, and the minimum thickness of the overhang, measured from a reference point of the upper surface thereof, is equal to or less than 2 times the predetermined distance.

Generally, the predetermined distance may be construed as a characteristic transverse dimension of filaments to be held by the hooks. For example, the predetermined distance can be a nominal diameter of the retaining filaments, such as, e.g., diameter D shown in FIGS. 16-17.

In addition, the predetermined distance may be a function of diameter D.

Typically, the predetermined distance may correspond to the average diameter of the filaments intended to be captured under the hooks. More generally, the predetermined distance may be the average largest diametric distance measured on the filaments of the counterpart.

Even more generally, and because the retaining filaments may have cross sectional shapes other than circular shapes (e.g., oval or flat), the predetermined distance may be construed as the average largest cross-sectional length of the retaining filaments.

Accordingly, the predetermined distance may be the diametric dimension of a typical filament, and the diameters of the other filaments of the counterpart may generally vary in a ±10 percent range with respect to this diametric dimension.

The predetermined distance is preferably comprised between 5 and 150 microns, more preferably between 15 and 25 microns. As far as hygiene products are concerned, in particular products intended to be put in contact with a person's skin, such as a baby, the diameter of the filaments is usually small to avoid abrasive feel, discomfort or injury. In this case, the diameter of the filaments is preferably comprised between 15 and 25 microns. In other technical applications, for example civil engineering, it may be necessary to have thicker filaments, notably to obtain a high resistance of the mechanical fastening.

The hook fastener according to the present invention includes a base strip and gripping hooks, each gripping hook having a stem extending from the base strip and a head or cap with at least one overhang or arm projecting past the stem and over the base strip.

In the entire present description, the main direction of a gripping hook should be considered as the direction in which it protrudes from the base strip. Accordingly, the main direction of the gripping hook corresponds to the central axis thereof, or, more generally, to the central axis of the stem.

The lateral direction of a gripping hook may be considered as the direction which is contained in a median plane defined between the two opposed surfaces delimiting the gripping hook at the cap portion thereof, and which, further, is perpendicular to the main direction of the gripping hook defined hereabove.

The transverse direction of a gripping hook should be considered as a direction perpendicular to both the main and lateral directions.

If the hooks are formed by extrusion, the transverse direction may also be considered as the extruding direction, while the lateral direction is perpendicular to said direction and the main direction of the hook.

In the present description, it will further be considered that the overhang extends laterally from the top of the stem, the top of the stem being defined at the top end of the narrowest portion of the hook.

The overhang has a swelling generally located near the distal end thereof, and forms, with its underside, a retaining cavity for the filaments.

The minimum thickness of the overhang, the cavity width and the cavity depth have proved to be key parameters for defining the optimal shape of a gripping hook.

The minimum thickness of the overhang is measured in an intermediate region located between the swelling of the overhang and the hook stem.

Generally, this minimum thickness is measured from a particular point on the upper surface of the overhang, in a direction which is perpendicular to a direction extending tangentially to this upper surface (at this particular point).

As an example, the minimum thickness may be measured in the median plane defined between the two opposed surfaces delimiting the gripping hook at the cap portion thereof. It may also be measured in a plane perpendicular to the transverse direction of the hook, notably when the hook is made by extrusion.

This intermediate region is thus thinner and so flexible. When a force is applied to the distal end portion of the overhang, this distal end portion will slightly bend upwards or downwards with respect to a flexion point located at the intermediate region.

This bending of the overhang plays a key role when the hook fastener is applied on its female counterpart and when it is released therefrom, because it allows the filaments to easily penetrate in the cavity and to safely escape therefrom without being broken.

The swelling, on the other hand, resists deformation of the overhang when the filaments captured in the cavity are put under tension and apply a force on the intermediate region of the overhang. In this case, the flexion point of the overhang is transferred in the vicinity of the stem which has a sufficient rigidity to prevent undue deformation of the overhang. The overhang possibly bends upwards, but not enough for the filaments to be released from the overhang's underside.

The cavity or recessed portion formed on the underside of the overhang is sufficiently wide to capture at least one filament, and sufficiently deep to keep the filaments from escaping laterally from the gripping hook.

The cavity width is measured in the lateral direction of the gripping hook, between a low point of the bottom surface of the overhang and the facing part of the gripping hook. The facing part of the gripping hook may be the lateral surface of the stem, which may be planar or curved, adjacent the overhang. According to another example, it may be an opposite part of the overhang itself, for example when the narrower portion of the stem is lower than the above defined low point.

In the entire present description, the low point of the bottom surface of the overhang will be defined as the lowest point of the overhang, in the main direction of the hook, being located on the exterior side of the overhang.

The low point may be defined in the median plane between the two opposed surfaces delimiting the gripping hook at the cap portion thereof.

The cavity depth is measured in the main direction of the gripping hook, between the low point of the bottom surface of the overhang and a high point of said surface.

In the entire present description, the high point of the bottom surface of the overhang will be defined as the highest point of said surface, in the main direction of the hook, being located in the vicinity of the intermediate region.

The high point may be defined in the median plane between the two opposed surfaces delimiting the gripping hook at the cap portion thereof.

It should be noted that the retaining filaments, with which the gripping hooks may mate, are not limited in their arrangement and form. In other words, the counterpart should not been limited to a nonwoven material (although the present invention is seen as particularly suitable therefor), and should also be envisaged as any other loop fastener material, for instance woven or knitted material.

In the present description, the effective width of the overhang will be measured in the lateral direction of the gripping hook, between the farthest outboard point of the overhang and the projection of the low point on the facing surface of the gripping hook, in said lateral direction. Preferably, this effective width is between 3 and 5 times the predetermined distance (discussed above). A width in this order enables a certain flexibility of the overhang while ensuring that the cap still passes through the counterpart material.

The farthest outboard point of the overhang may be measured in the median plane defined between the two opposed surfaces delimiting the gripping hook at the cap portion thereof.

The minimum thickness of the overhang is advantageously equal to or greater than 0.5 times the predetermined distance, and more preferably equal to or greater than 0.8 times said predetermined distance. This ensures that the overhang is not too flexible at its intermediate region and keeps a relative rigidity, which is needed to prevent undue bending thereof and release of the captured filaments.

It should be noted that, in the present description, the maximum thickness of the overhang is measured in the swelling, in the main direction of the gripping hook, between the upper and the lower surface of the overhang. Generally, the maximum and the minimum thickness of the overhang may be measured in directions which are parallel or substantially parallel, notably inclined with respect to one another by an angle smaller than 30°.

The maximum thickness of the overhang may be measured as from a point of the upper surface of the overhang which is included in the median plane defined between the two opposed surfaces delimiting the gripping hook at the cap portion thereof to the lower surface of the overhang.

In certain embodiments, the maximum thickness of the overhang is at least equal to the sum of the minimum thickness and half of the predetermined distance, and is less than 5 times the predetermined distance.

In certain embodiments, the ratio between the gripping hook overall height, measured from the top thereof to the base strip in the main direction of the gripping hook, and the thickness of the base strip measured in said main direction, is between 3 and 12. This ensures that the gripping hooks have a sufficient height to reach into the counterpart material, and that the base strip has a minimum thickness and thus a relative rigidity, allowing that the gripping hooks be kept upright when pressed into the counterpart material.

In certain embodiments, the effective cap height, measured in the main direction of the gripping hook, from the top of the gripping hook to the low point of the overhang, is comprised between 30 and 200 microns. Preferably, the effective cap height is less than or equal to 120 microns. The effective cap height should indeed be short enough to prevent the cap from bottoming out against the counterpart backing.

In certain embodiments, notably when the hook is made by extrusion, the depth measured in the main direction of the hook, between the projection in the same direction of the reference point on the bottom surface of the overhang, and the low point of the overhang, is comprised between 0.25 and 1 times the cavity depth. The slope on which the captured filaments slip to leave the hook is thus smooth, which prevents fuzzing.

The same advantage is obtained when a straight line connecting the low point of the overhang and the projection of the reference point, in the main direction of the hook, on the bottom surface of the overhang, forms an angle comprised between 30 and 90° with a plane perpendicular to the general axis of the hook.

In certain embodiments, the base strip and the gripping hooks are made of a material comprising at least 70% by mass of a polyolefin, preferably polypropylene.

In certain embodiments, the bottom surface of the overhang includes a concave surface part located on the stem side and a convex surface part extending said concave surface part from an inflection point towards the distal end of the overhang.

In certain embodiments, the upper surface of the overhang is flat or convex at least in a region which is delimited by a first plane containing the innermost point of the stem adjacent to the overhang and a second plane containing the inflection point, said first and second planes being perpendicular to the lateral direction.

This allows the filaments to slide off the cap and penetrate the retaining cavity of the gripping hook when the hook fastener is pressed against the counterpart material.

In certain embodiments, the minimum thickness of the overhang is measured between a first plane containing the innermost point of the stem adjacent to the overhang and a second plane containing the inflection point, said first and second planes being perpendicular to the lateral direction.

The innermost point of the stem adjacent to the overhang and the inflection point may for example be defined in the median plane between the two opposed surfaces delimiting the gripping hook at the cap portion thereof.

Preferably, the cavity depth is less than 2 times the predetermined distance, which ensures that the filaments are not stuck in the cavity upon opening of the mechanical fastener.

In certain embodiments, the cap of the gripping hook includes two overhangs which are laterally opposed.

In certain embodiments, the top of the gripping hook is laterally offset with respect to the central axis of the stem while remaining in the area bounded by a plane containing the innermost point of the stem adjacent the overhang and perpendicular to the lateral direction of the gripping hook.

In certain embodiments, the half-width of the stem, measured in the lateral direction at its narrowest portion, is comprised between 2 times the minimum thickness of the overhang and 3 times the maximum thickness of the overhang.

It is to be understood that, except in cases of obvious incompatibility and unless otherwise stated, features of one embodiment or example described herein can similarly be applied to other embodiments or examples described herein.

Other features and advantages of the invention will become apparent from the following detailed description, taken in conjunction with the accompanying drawings, which illustrate, by way of example, the principles of the invention.

BRIEF DESCRIPTION OF THE DRAWINGS

In the drawings, like reference signs generally refer to the same parts throughout the different views.

DETAILED DESCRIPTION

The following detailed description refers to the accompanying drawings showing examples of hook fasteners according to the present invention. It is intended that these examples be considered as illustrative only, the scope of the invention not being limited thereto.

Figure 1:
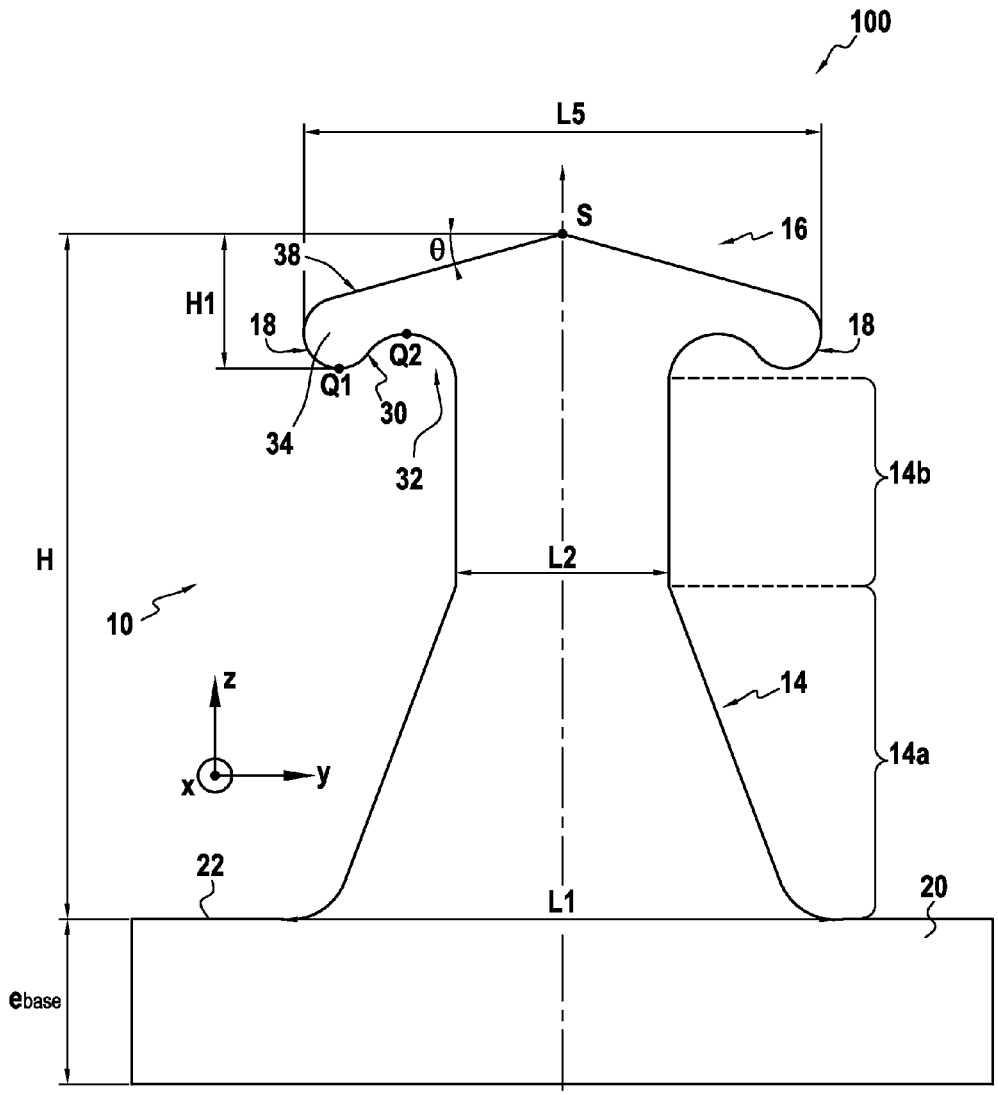
FIG. 1 is a partial side view of a hook fastener according to a first embodiment of the present invention, along the direction x shown in FIG. 13.
Figure 2:
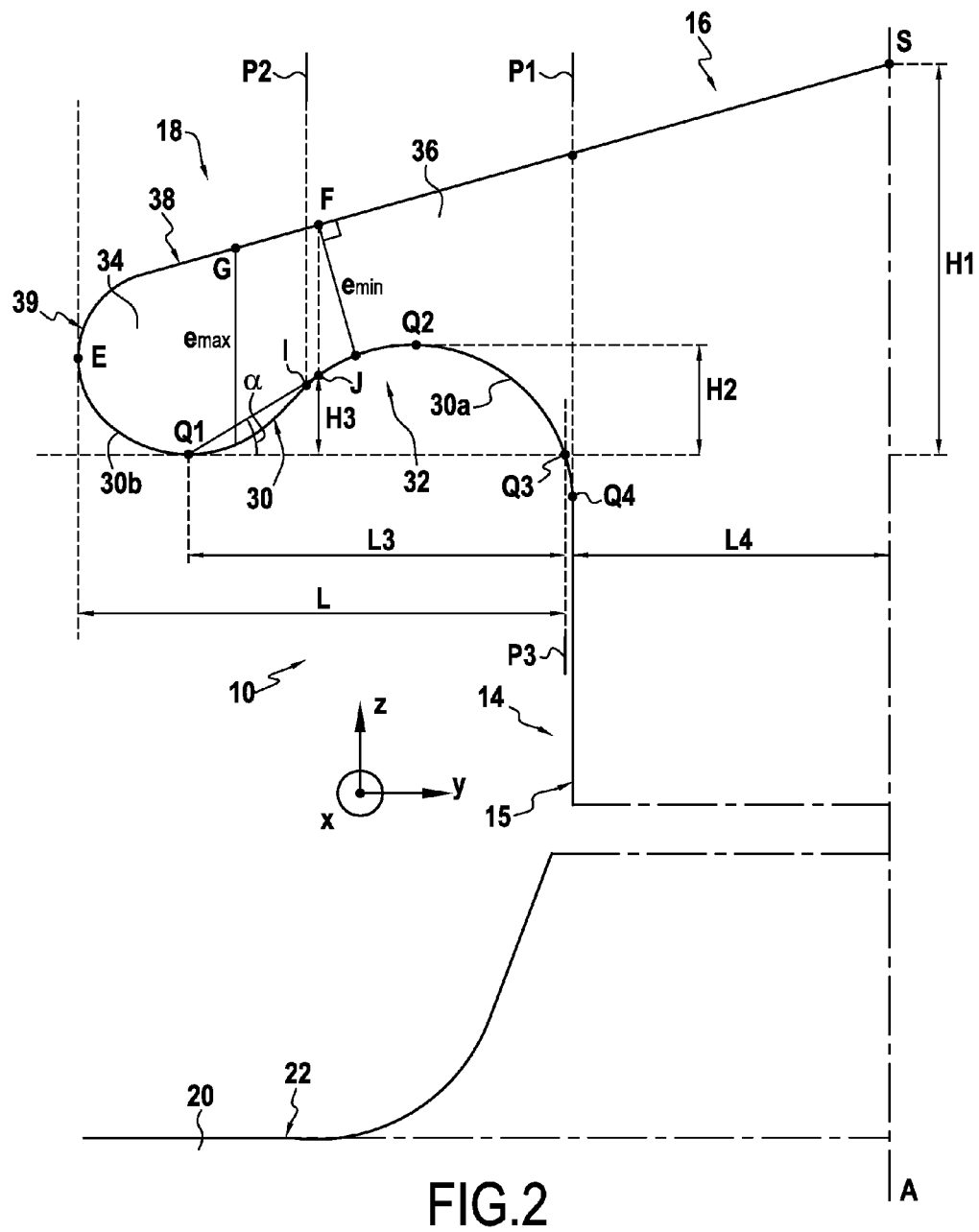
FIG. 2 is an enlarged view of an overhang of the gripping hook illustrated in FIG. 1.
Figure 13:
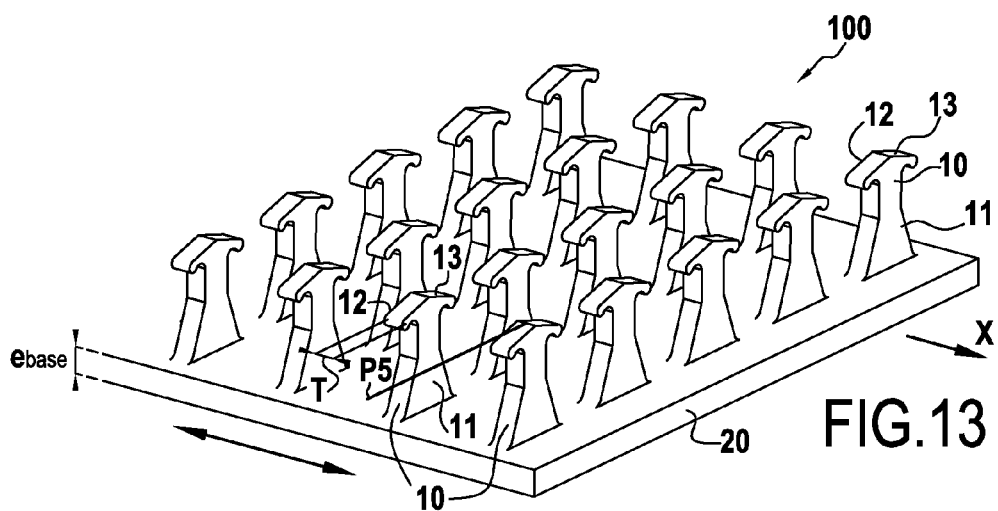

For the sake of simplicity of the description, FIGS. 1 and 2 only show a part of a hook fastener 100 according to a first embodiment of the present invention. The hook fastener 100 as a whole is illustrated in FIG. 13.

Figure 14:
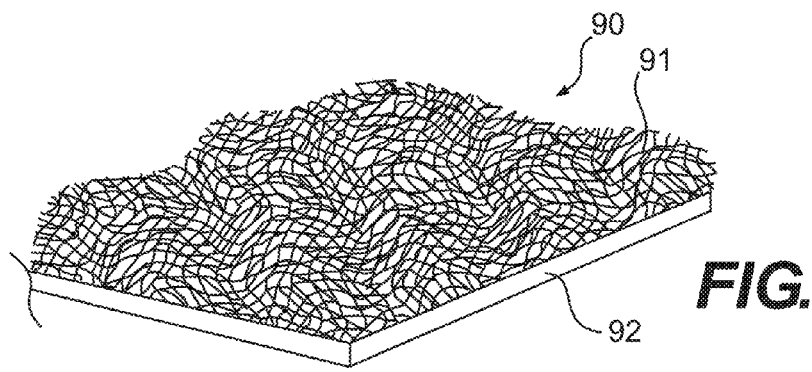
FIG. 14 is a perspective view of a female counterpart adapted to cooperate with a hook fastener according to the present invention.

This hook fastener 100 is, for example, intended to cooperate with a nonwoven counterpart 90 comprising interlaced filaments 91 arranged on a backing 92, as shown in FIG. 14.

The interlaced filaments 91 are characterized by their nominal diameter D, to which it will be referred in the following description. For example, the nominal diameter D of the filaments corresponds to the largest length measured among the filaments 91, in their cross sectional direction. It is advantageously comprised between 5 and 150 microns, and more preferably between 15 and 25 microns. Preferable values and ranges for the dimensions of the hook will be defined hereunder with respect to this nominal diameter D.

According to another embodiment of the invention, the backing 92 may be omitted.

As shown in FIG. 13, the hook fastener 100 comprises a base strip 20 and a plurality of gripping hooks 10 protruding from the strip 20, the whole being made of conventional thermoplastic material, such as polypropylene.

It should be noted that, according to other embodiments, a hook fastener according to the invention may comprise gripping hooks 10 as will be defined hereinafter and, in addition, other different hooks.

In the illustrated example, however, the hook fastener comprises exclusively gripping hooks 10. Consequently, for the sake of simplicity, the gripping hooks 10 will be referred to as hooks in the following description.

In the present example, the hooks 10 are arranged in rows which are mutually parallel.

Advantageously, the hook fastener 100 may have a hook density of 10 to 1000 hooks per square centimeter.

Each hook is delimited by a front side 11 and a back side 12, which, in the present example, are constituted by two opposed surfaces that are planar and parallel or substantially parallel to each other. The front and back sides 11, 12 are adjoined by a side edge 13 as shown in FIG. 13.

In the example, the hook 10 extends, between its front and back sides 11, 12, perpendicularly to said sides 11, 12.

Referring now to FIG. 1, which shows a side view of a hook as defined hereabove in a direction perpendicular to its front and back sides, the hook 10 comprises a stem 14 extending generally upwards from the base strip 20.

As further shown in FIG. 1, the stem 14 has a central axis A extending in a main direction z which is the direction in which the stem 14 protrudes from the base strip 20 and which will be referred to hereinafter as the main direction of the hook 10. In the example, the main direction z is perpendicular to the upper surface 22 of the base strip 20.

The stem 14 is further topped by a cap 16.

Generally, heights will be measured in the main direction z of the hook and widths will be measured in the lateral direction y thereof.

Figure 18:
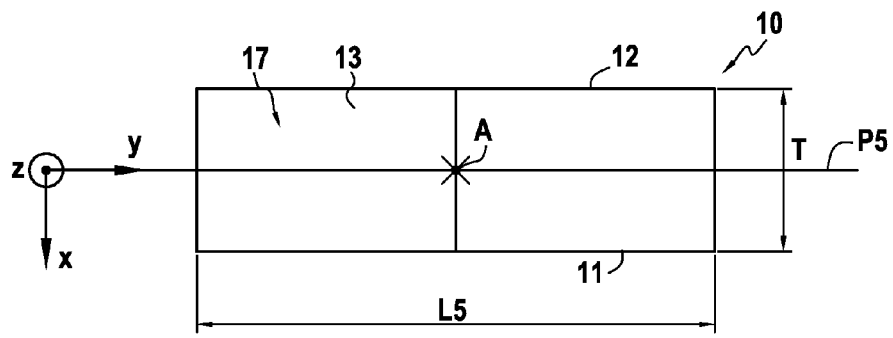
FIG. 18 is a top view of the gripping hook of FIG. 1.

For the following description, the lateral direction of the hook will be defined as a direction which is perpendicular to the main direction z, and which is included in a median plane P5 between the front and back sides 11, 12 of the hook 10 (see for instance FIGS. 13 and 18.

Generally, the width dimensions which will be mentioned hereinafter will be considered measured in this lateral direction.

In the illustrated example, the lateral direction y is also parallel to the upper surface of the base strip 20 and perpendicular to a junction line between the intermediate surface 13 and the upper surface of the base strip 20.

In the illustrated example, the hook 10 extends, between its front and back sides 11, 12, in a direction which will be referred to as the transverse direction x, and said front and back sides 11, 12 are perpendicular to this direction. In the present example, this direction x further corresponds to the direction of the rows mentioned with reference to FIG. 13 or, more particularly, to the extrusion direction if the hook is made by extrusion.

The transverse direction of the hook is perpendicular to both the main and lateral directions z, y.

The thickness T of the hook 10 is defined here as the distance between the front and back sides 11 and 12 in this transverse direction x. Preferably, the hook thickness T will be between 200 and 270 microns.

When viewed from the top in the main direction z (in other words when projected in a plane perpendicular to the main direction z), the hook cap 16 defines an effective engagement area 17 which here has a rectangular overall shape as illustrated in FIG. 18. The size of this area is preferably between 40 000 and 120 000 square micrometers, more preferably between 50 000 and 100 000 micrometers, and still more preferably between 60 000 and 85 000 micrometers. It should be noted that, according to another example, the effective engagement area may also have a parallelepiped-shape, the angles between two adjacent sides of the parallelepiped being different from 90°.

In order to improve stability of the hook, the stem 14 has preferably a maximum width in a region which is nearer from the base strip 20 than from the cap 16. In particular, the stem 14 has preferably its maximum width at the junction with the base strip 20 or in the vicinity of the base strip 20, at a small distance thereof. That is, the stem 14 is flared towards the base strip 20.

In the example illustrated in FIG. 1, the stem 14 comprises a lower portion 14a which width decreases from a maximum value L1 at its lower end attached to the base strip 20 to a minimum value L2, and an upper portion 14b, having a substantially constant width L2, located between this lower portion 14a and the cap 16. The funnel-shaped lower portion 14a of the stem 14 confers high stability to the hook 10, keeping it upright when the hook fastener 100 is pressed against the counterpart 90. The maximum width L1 of the stem is preferably between 150 and 250 microns, and the minimum width L2, between 100 and 200 microns.

According to another example, the lateral surfaces 15 of the stem 14 may be entirely curved.

Figure 10:
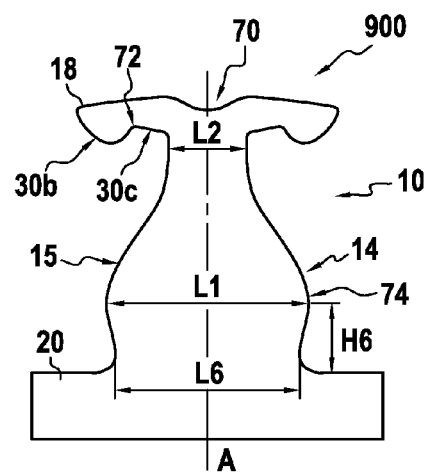

Another example is illustrated in FIG. 10, in which the stem 14 has a maximum width L1 in a region 74 located at a small distance H6 from its lower end, and gets narrower between this region 74 and the base strip 20. The minimum width of the stem 14, measured in its upper part, may preferably be less than two third of said maximum width L1, more preferably less than or equal to half of said maximum width L1. In the present example, preferably, the stem width L6 measured at the junction with the base strip 20 may be around 0.8 times the maximum width L1.

The overall height H of the hook 10 is measured from the highest point (top) S of the cap 16 in the main direction z to the upper surface 22 of the base strip 20. It is preferably between 350 and 550 microns. Also preferably, the ratio between the hook overall height H and the thickness $e_{base}$ of the base strip 20 is between 3 and 12.

As shown in FIG. 1, the cap 16 comprises two overhangs or arms 18 protruding from one side and the other of the stem 14, in the lateral direction y. These overhangs form engagement portions of the hook 10 which are intended to capture and retain the filaments 91 of the counterpart 90.

The effective cap height H1 is measured in the main direction z from the highest point S of the hook 10 to the lowest point Q1 of the overhang 18 (or of the overhangs, if there are more than one). Preferably, said effective cap height H1 is comprised between 30 and 200 microns. Still more preferably, the effective cap height H1 is less than or equal to 120 microns.

In the present example, the cap 16 has a peak and the highest point S of the cap is aligned with the central axis A of the hook. This, however, is not limitative, and the upper surface of the cap 16 may for example have a recess 70 in the vicinity of the central axis A, as illustrated in FIG. 10, or the center part of this surface 38 may be planar. This enables the effective cap height H1 to be smaller, which may facilitate the engagement of the hook through the filaments of the counterpart 90. In other embodiments, the cap 16 may have a rounded top, or a flat top, or any other shape known in the art or combinations of any of these.

The cap width L5 is measured between the outboard point of the left overhang and the outboard point of the right overhang, and is preferably between 280 and 400 microns.

The overhang 18 illustrated on the left of FIG. 1 will now be described in more detail in reference to FIG. 2.

Figure 15:
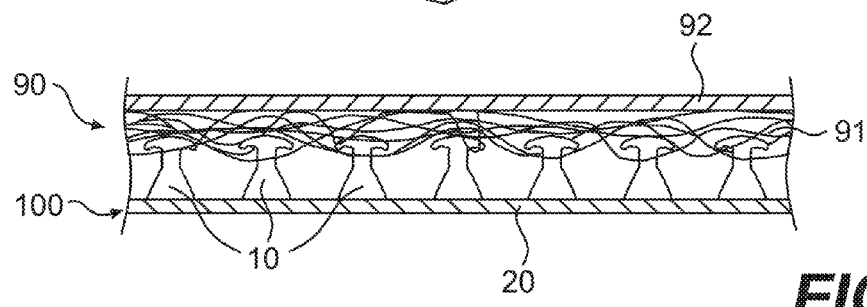
FIG. 15 is a side view of a hook fastener according to the present invention being pressed against the female counterpart of FIG. 14, the hook fastener and the female counterpart forming a mechanical fastener.

In the example, the upper surface 38 of the overhang 18 is substantially planar, but inclined downwards towards the distal end thereof. When the hook fastener is pressed against the counterpart 90, as shown in FIG. 15, the filaments 91 thus slide off the cap 16 and are directed towards the distal end and finally the underside of the overhang 18. Generally, the angle θ formed between the upper surface 38 of the overhang 18 and a plane perpendicular to the main direction z of the hook is preferably between 0° and 30°, more preferably between 0° and 10°, and still more preferably equal to 5°. This example however is not limitative, and the upper surface 38 of the overhang 18 may have a convex shape instead of being planar.

The upper surface 38 is terminated at its distal end by a curved surface 39 extending downwards to the bottom surface 30 of the overhang 18.

As shown in FIG. 2, the bottom surface 30 of the overhang 18 includes a concave surface part 30a located on the stem side, this concave surface part being continued, as from an inflection point I, by a convex surface part 30b extending towards the distal end of the overhang 18 and linked to the upper surface 38 at point E, which is the farthest outboard point of the overhang in the lateral direction. The above described structure results in a cavity 32 being formed on the underside of the overhang 18, the cavity 32 being intended to receive one or more filaments 91 of the counterpart 90 as will be described in more detail in reference to FIGS. 15 to 17.

A cavity width L3 is measured between the low point Q1 of the bottom surface 30 of the overhang 18 located in the convex surface part 30b, and the projection Q3 of said low point Q1 on the facing surface of the hook, in said lateral direction. The cavity width L3 is preferably equal to at least 2 times the nominal diameter D.

A cavity depth H2 is measured between the low point Q1 and a high point Q2 of the bottom surface 30 located in the concave surface part 30a. Preferably, the cavity depth H2 is equal to or greater than 0.4 times the nominal diameter D. Even more preferably, the cavity depth H2 is still less than 2 times the nominal diameter D.

An effective width L of the overhang 18 is measured between its farthest outboard point E and the projection Q3 of the low point Q1 on the facing surface of the hook, in said lateral direction. This effective width L is preferably comprised between 3 and 5 times the nominal diameter D of the filaments.

Consequently to the above structure, the overhang 18 comprises a swelling 34 located at a distance from the stem 14, and a thinner intermediate region 36 located between said swelling 34 and the stem 14, the retaining cavity 32 being located in the vicinity of this intermediate region 36.

The swelling 34 is configured so that the thickness of the overhang 18 increases therein from the intermediate region 36 towards the distal end of the overhang 18. The thickness of the overhang 18 may for example be measured in a direction perpendicular to the upper surface 38 thereof.

In the illustrated example, when the thickness of the overhang 18 is continuously measured, in a direction perpendicular to the upper surface 38 thereof, from its proximal end adjacent the stem 14 towards its opposed distal end, this thickness takes a first minimum value $e_{min}$ at a reference point F located in the intermediate region 36 and then increases again.

Preferably, the minimum thickness $e_{min}$ of the overhang is measured between a first plane P1 containing the innermost point Q4 of the stem 14 adjacent to the overhang 18 and a second plane P2 containing the inflection point I, both first and second planes being perpendicular to the lateral direction y. In the example, the first plane P1 contains the planar lateral surface 15 of the stem 14 adjacent to the overhang 18.

Still more preferably, the minimum thickness $e_{min}$ of the overhang may be measured between a plane P3 perpendicular to the lateral direction y and containing the projection Q3 of low point Q1 on the facing side of the hook in that lateral direction, and the second plane P2 as hereabove defined.

Advantageously, the minimum thickness $e_{min}$ of the overhang is equal to or less than 2 times the nominal diameter D. More preferably, this minimum thickness $e_{min}$ is less than 1.5 times the nominal diameter D. Also preferably, the minimum thickness $e_{min}$ is equal to or greater than 0.8 times the predetermined distance.

A maximum thickness $e_{max}$ of the overhang may further be measured, in the main direction z of the hook, from a point G of the upper surface 38 of the overhang 18 which is nearer from the distal end of the overhang than reference point F, to an opposite point of its lower surface 30.

Advantageously, the maximum thickness $e_{max}$ of the overhang is at least equal to the sum of the minimum thickness $e_{min}$ and half of the predetermined distance.

Further preferably, the maximum thickness $e_{max}$ of the overhang is less than 5 times the predetermined distance.

In the present example, the minimum and maximum thicknesses of the overhang are measured in directions forming a slight angle with each other. Generally, both measurement directions may be either parallel or substantially parallel to each other, or slightly inclined with respect to each other.

Advantageously, the half-width L4 of the stem 14, measured at its narrowest portion (here in the vicinity of cap 16), is preferably between 2 times the minimum thickness $e_{min}$ of the overhang and 3 times the maximum thickness $e_{max}$ of the overhang 18.

The behavior of the above described structure upon utilization with a female counterpart as shown in FIG. 14 will now be explained in reference to FIGS. 15 and 17.

FIG. 15 shows a mechanical fastener comprising a counterpart 90 as illustrated in FIG. 14 and a hook fastener 100 as described above, in a state in which the hook fastener 100 is pressed against the counterpart 90 for engaging its hooks 10 with the filaments 91.

The small thickness of the overhang 18 at its intermediate portion 36 allows the distal end of the overhang 18 to bend with respect to a flexion point located in the vicinity of this intermediate region 36, and thus allows the overhang to easily penetrate in the counterpart material and between the filaments 91.

One retaining cavity 32 of a hook 10 can capture one or more filaments.

Figure 16:
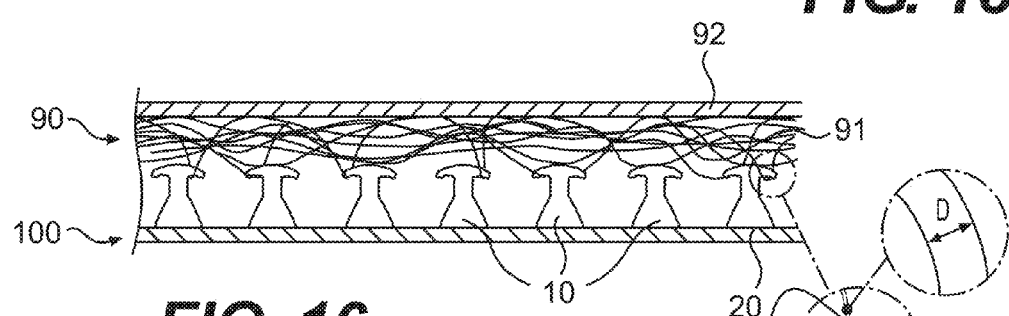
FIG. 16 is a side view showing the hook fastener of FIG. 15, in a closed state.

FIG. 16 shows the mechanical fastener of FIG. 15 in a closed state in which the filaments 91, captured in the cavities 32, are put under tension in a direction substantially perpendicular to the main plane of the mechanical fastener.

The swelling 34 prevents the overhang 18 from being excessively deformed due to the force applied on its intermediate region 36 by the tensioned filaments. The overhang slightly bends upwards, but not enough for the filaments 91 to be released from the overhang's underside 30. The flexion point of the overhang is moved into the vicinity of the stem 14 which has a sufficient rigidity to prevent undue deformation of the overhang.

Figure 17:
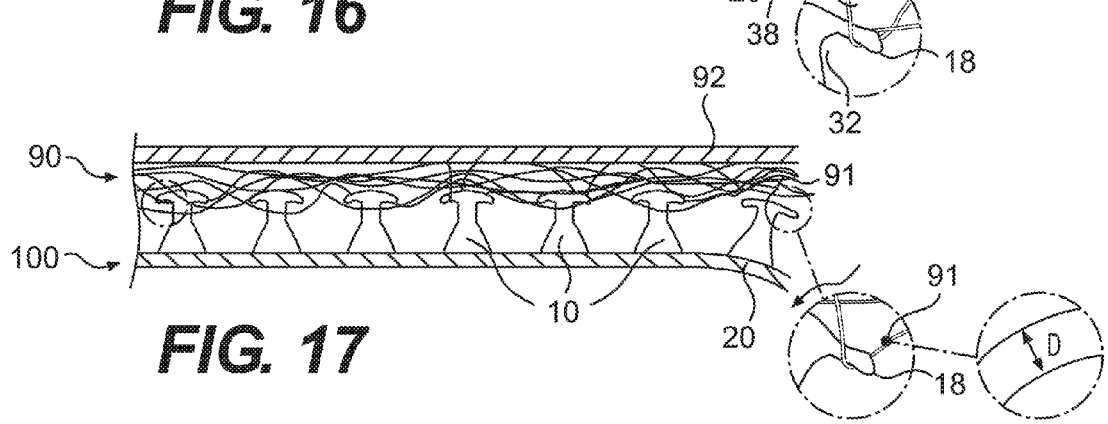
FIG. 17 is a side view of the mechanical fastener of FIG. 15, the hook fastener being peeled off from the counterpart for opening the mechanical fastener.

FIG. 17 shows peeling-off of the hook fastener 100 to open the mechanical fastener of FIGS. 15 and 16.

Under a peeling force, the filaments 91 are easily directed out of their cavity 32 due to the bottom surface 30 of the overhang forming a smooth slope (between the low point Q1 and the high point Q2).

Referring again to FIG. 2, this smooth slope is obtained for example when a depth H3 measured between the projection J in the main direction z of the reference point F on the underside 30 of the overhang 18, and the low point Q1 of the overhang 18, is between 0.25 and 1 time the cavity depth H2.

As a variant, this smooth slope is obtained when a straight line connecting the low point Q1 of the overhang and the projection 3 of reference point F, in the main direction z of the hook 10, on the bottom surface of the overhang, forms an angle α between 30 and 90° with a plane perpendicular to the main direction z.

As shown in the enlarged part of FIG. 17, the tensioned filament located at the outboard edge of the cavity then pushes on the distal end of the overhang 18 so that the overhang 18 bends upwards around a flexion point located in the flexible intermediate region 36. The filaments 91 are thus smoothly released out of cavity 32, and breaking thereof is efficiently avoided.

As a non-limitative example, a hook fastener according to the present invention may have following dimensions: a base strip 20 having a thickness $e_{base}$ of 100 microns, an overall height H of the hook of 450 microns, an effective cap height H1 of 50 microns, an overall width of the cap 16 of 360 microns, a total width L of the overhang 18 of 95 microns, a maximum width L1 of the stem 14 of 290 microns, a minimum width L2 of the stem 14 of 160 microns, a hook thickness T of 215 microns, a cavity depth H2 of 15 microns, a cavity width L3 of 60 microns, a minimum thickness $e_{min}$ of the overhang of 30 microns, and a maximum thickness $e_{max}$ of the overhang of 50 microns.

The hook fastener 100 of the present invention may be produced in accordance with the method described in the U.S. Pat. No. 4,056,593, referred to below as the De Navas or Repla method.

Figure 11:
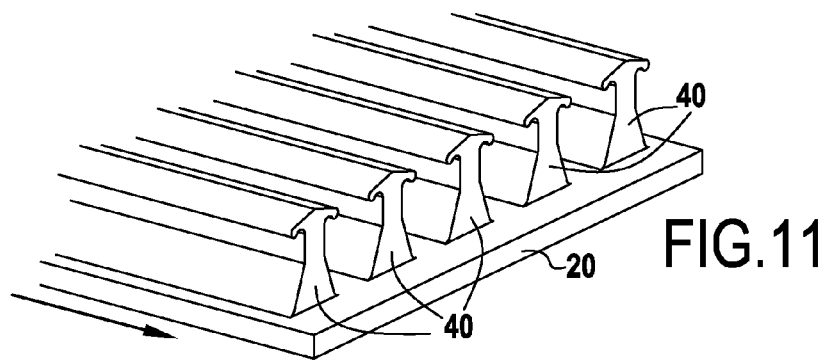
FIGS. 11 to 13 illustrate different steps of a process for forming a hook fastener according to the invention.

As illustrated in FIG. 11, the De Navas or Repla method includes a step of extruding a thermoplastic resin through a die (not represented) shaped to form a base strip 20 and spaced ridges 40 projecting above an upper surface 22 of the base strip 20, each ridge 40 having the cross sectional shape of the hooks to be formed.

Figure 12:
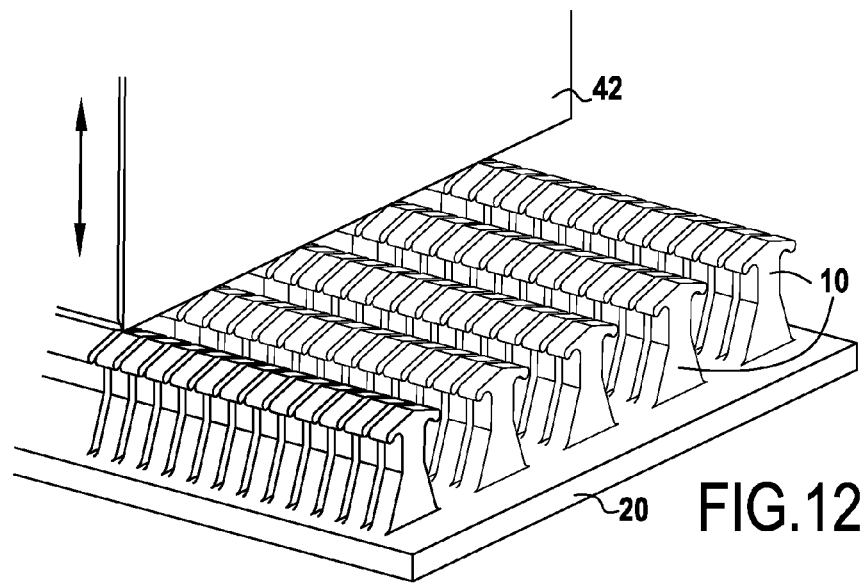

In a further step of the process which is illustrated in FIG. 12, the ridges 40 are cut transversally with a knife 42, at spaced location along their length, the space between two cuttings corresponding to the desired thickness T of the hooks 10.

In a third step illustrated in FIG. 13, the base strip 20 is then stretched to separate the cut portions of the ridges 40, thus forming rows of hooks 10 having the desired structure.

In the illustrated example, the ridges are cut perpendicularly to the general direction thereof (i.e. the extrusion or machine direction). The knife is here for defined in a plane which is normal to this machine direction.

According to an alternative embodiment, the knife may also cut the ridges along a plane which is slightly inclined with respect to that normal plane, around the z-axis, for example through an angle of from 10° to 30°. In that case, after stretching the base strip, the hooks from one row may be offset in the extension direction of the rows, relative to the hooks of an adjacent row. It should be noted that the effective engagement area defined by the cap in this case generally has a lozenge shape.

According to still an alternative embodiment, the knife may cut the ridges along a plane which is slightly inclined with respect to a plane normal to the machine direction, around the y-axis, for example through an angle of from 10° to 30°. In this case, the opposed surfaces 11, 12 of each hook are no more perpendicular to the extrusion direction, but inclined around the y-axis with respect to a plane perpendicular to the extrusion direction. Hence, the main direction z of each hook is tilted with respect to a direction perpendicular to the base strip 20.

Both aforementioned alternative embodiments may also be combined.

The De above described method is given only as an example. Any other suitable method may be used by the skilled person to obtain a hook fastener according to the present invention. An example of an alternative method is disclosed in the already mentioned US Patent Pub No. 2004/0068848. The claimed hook fastener may also be obtained by molding, suitable molding methods being disclosed in international publication WO 92/15262, U.S. Pat. No. 3,196,490 and U.S. Pat. No. 4,775,310. A hook fastener according to the present invention may further be obtained by coextrusion or by extrusion and coating or coextrusion and coating.

Other embodiments of the present invention will now be described with reference to FIGS. 3 to 10.

Figure 3:
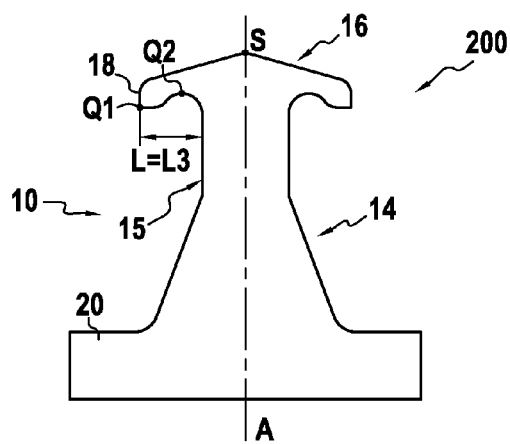
FIGS. 3 to 10 are partial side views of hook fasteners according to other embodiments of the present invention.

FIG. 3 illustrates a part of a hook fastener 200 according to a second embodiment of the present invention. According to this embodiment, the low point Q1 of the bottom surface 30 of the overhang 18 is a farthest outboard point of the overhang 18. Consequently, the total width L of the overhang 18 is equal to the cavity width L3 measured between said low point Q1 and the lateral surface 15 of the stem 14.

Figure 4:
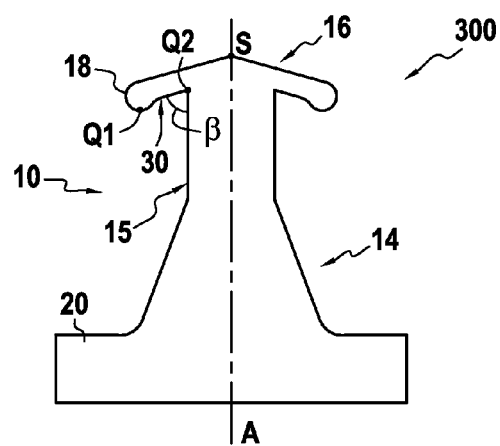

FIG. 4 illustrates a part of a hook fastener 300 according to a third embodiment of the present invention, in which the high point Q2 of the bottom surface 30 of the overhang 18 is located at the junction of this bottom surface 30 with the lateral surface 15 of the stem 14 adjacent said overhang 18. In other words, at the junction point between the bottom surface 30 of the overhang 18 and the lateral surface 15 of the stem 14, the tangent to the bottom surface 30 and the tangent to the lateral surface 15 are not collinear and define an angle β, as shown on the figure.

Figure 5:
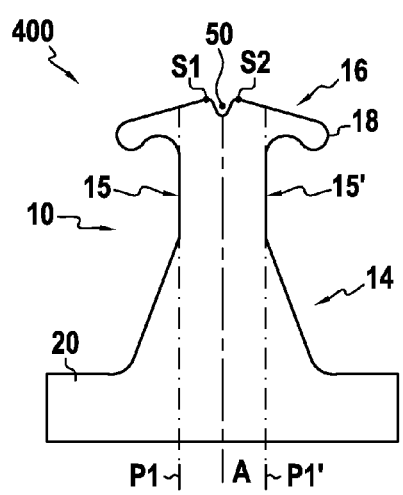

FIG. 5 illustrates a part of a hook fastener 400 according to a fourth embodiment of the present invention. According to this embodiment, the hook 10 has two tops S1 and S2 separated by a recess 50, each top S1, S2 being offset with respect to the central axis A of the stem while remaining in the area bounded by the two planes P1, P1' respectively containing a lateral surface 15, 15' of the stem 14.

Figure 6:
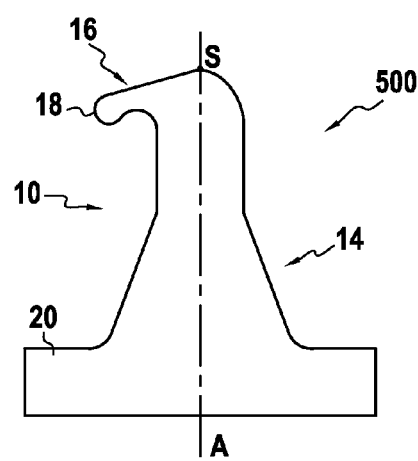

FIG. 6 illustrates a part of a hook fastener 500 according to a fifth embodiment of the present invention. According to this embodiment, the hook 10 comprises only one overhang 18 protruding at one lateral side of the hook 10.

Figure 7:
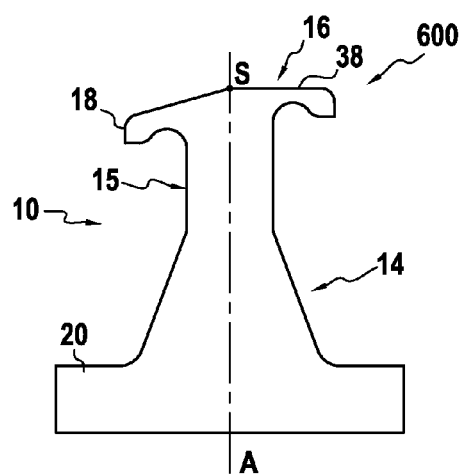

FIG. 7 illustrates a part of a hook fastener 600 according to a sixth embodiment of the present invention. According to this embodiment, the hook 10 is not symmetrical with respect to a plane perpendicular to the lateral direction y and including the center axis A of the stem 14. That is, the left and right overhangs have different configurations. The left part of the hook 10 remains the same as that described with reference to any other embodiment of the present invention, while its right part is slightly lifted upwards such that the upper surface 38 of the cap 16 extends substantially horizontally.

Figure 8:
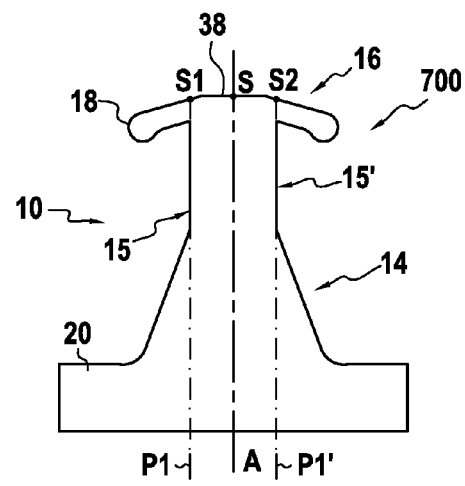

FIG. 8 illustrates a part of a hook fastener 700 according to a seventh embodiment of the present invention. According to this embodiment, the upper surface 38 of the cap 16 is flat in a region extending between a first point S1 and a second point S2, the first and second points S1, S2 being located respectively in the plane P1 comprising the left lateral surface 15 of the stem 14 and the plane P1' comprising its right lateral surface 15'.

Figure 9:
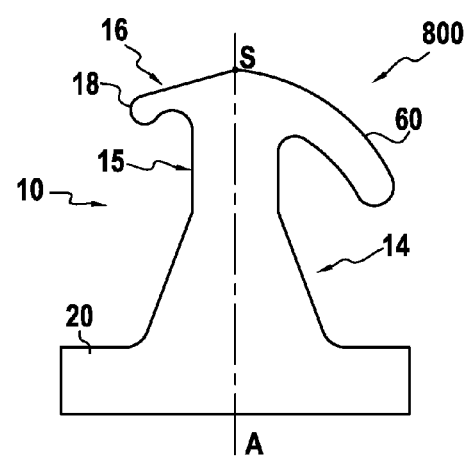

FIG. 9 illustrates a part of a hook fastener 800 according to an eighth embodiment of the present invention, in which the hook 10 comprises, on one side, an oversized projection 60 extending generally downwards, for example on half of the overall height H of the hook 10.

FIG. 10 illustrates a part of a hook fastener 900 according to a ninth embodiment of the present invention, in which the bottom surface of the overhang 18 comprises a first planar surface 30c extending upwards from the stem 14, and a convex surface 30b linked to said planar surface 30c through a concave part 72 having a very small radius of curvature and extending towards the upper surface of the overhang 18, thus forming the swelling 34. The planar surface 30c and the convex surface 30b may also join at an angular point.

The above description is given by way of example, and not limitation. The various features of the embodiments or examples disclosed herein can be used alone or in varying combinations with each other, and are not intended to be limited to the specific combination described herein. Further, given the above disclosure, one skilled in the art could devise variations that are within the scope of the invention disclosed herein.

In the above described embodiments, the front and back sides of the hook are formed by planar opposed surfaces, which, moreover, are parallel or substantially parallel to each other.

According to another example of the present invention, one or both of the front and back sides of the hook may comprise a planar upper part at its cap portion and a planar lower part at its stem portion, the upper and lower part of one side being inclined with respect to each other.

Figure 19:
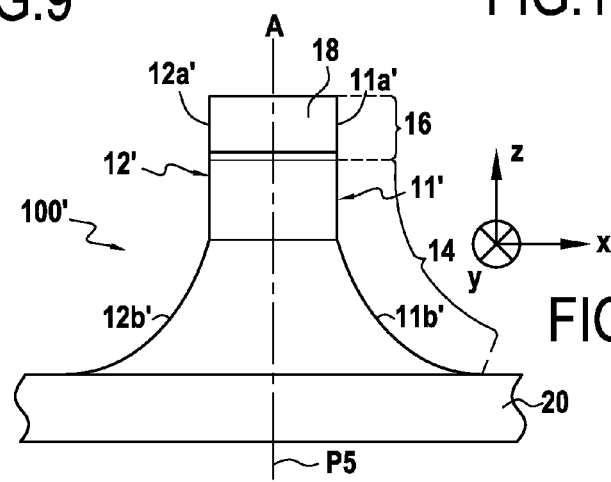
FIG. 19 is a partial side view of a hook fastener according to an alternative example of the present invention.

According to another example, one or both of the front and back sides of the hook may comprise a planar upper part at least at its cap portion and a curved lower part at its stem portion. This example is illustrated in FIG. 19, which shows a side view of a hook 100'. The front and back sides 11' and 12' of the hook 100' each comprise a planar upper part 11a', 12a' at the cap portion, and a curved lower part 11b', 12b' at the stem portion, such that the hook is gradually flared towards its lower end (i.e. towards the base strip).

It should be noted that the upper parts of the front and back sides of the hook, may also not be parallel or substantially parallel to each other.

As mentioned with reference to FIGS. 11 to 13, the front and/or back side 11, 12 of the hook may be inclined, for example through an angle of from 10° to 30°, with regard to a plane perpendicular to the transverse direction x thereof. Inclination thereof may occur either around the x- or the y-axis, or both.

In another example, only a part of each front and back sides 11, 12 may be inclined around the y-axis, said part being preferably located at the vicinity of the hook cap.

In still another example, the axis z, that is the main direction of the hook, may be slightly tilted on one or the other side with respect to a direction perpendicular to the base strip. That is, the hook may be tilted around the x-axis in one or the other direction with respect to a direction perpendicular to the base strip.

Although polypropylene is cited as an example of material for composing the hook fastener according to the present invention, any other suitable material could be used, preferably one comprising at least 70% by mass of a polyolefin (e.g. polyethylene, polypropylene, polybutylene and the like). Polyamides (e.g. nylon 6, nylon 6/6, nylon 10, nylon 12 and the like); polyesters (e.g. polyethylene terephthalate, polybutylene terephthalate, polylactic acid and the like); polycarbonate; polystyrene; thermoplastic elastomers; vinyl polymers; polyurethane; as well as blends and copolymers thereof may also be used. Various renewable materials, including bioplastics derived from renewable biomass sources such as cellulose, biopolymers, etc. may further be used.

In the illustrated example, the hooks are made of the same material and in a single piece with the base strip. In alternate embodiments, the hooks and the substrate may be formed separately. In other embodiments, the hooks and the substrate may also be made from two or more different materials. In this case, the hook fastener may be formed, for example, by coextrusion or extrusion and coating or coextrusion and coating.

It is further contemplated that any of the embodiments of the present disclosure can be configured as described in US patent application number, entitled "Absorbent articles with hook and loop fastening systems", filed Nov. 10, 2011 by The Procter & Gamble Company in the name of Nayda RamosMedina, et al., which is hereby incorporated by reference. Any hook fastener (including any hook configurations) and any female counterpart disclosed herein can be configured as described therein.

The invention claimed is:

1. A hook fastener, adapted to be attached to a counterpart comprising retaining filaments by a cooperation of its hooks with said filaments, including:
   a base strip, and
   a field of hooks comprising gripping hooks protruding from said strip, each said gripping hook comprising a stem which extends in its main direction and is topped by a cap, said cap including at least one overhang extending laterally from said stem, and each said gripping hook being further delimited, at least at its cap portion, in its transverse direction, by two opposing substantially planar surfaces,
   wherein the overhang comprises a swelling located at a distance from the stem so that a thickness of the overhang increases in said swelling from an intermediate region of the overhang located between said swelling and said stem in a direction towards a distal end of the overhang, a bottom surface of the overhang forming a cavity for receiving the filaments of the counterpart in a vicinity of said intermediate region, a cavity width measured in a lateral direction of the gripping hook, between a low point of the bottom surface of the overhang and a facing part of the gripping hook, is equal to at least 2 times a predetermined distance, wherein the predetermined distance is an average largest cross-sectional dimension of the retaining filaments, a cavity depth measured in the main direction of the gripping hook, between the low point of the bottom surface of the overhang and a high point of the bottom surface of the overhang, is equal to or greater than 0.4 times the predetermined distance and is less than 2 times the predetermined distance, and a minimum thickness of the overhang, measured from a reference point of an upper surface thereof, is equal to or less than 2 times the predetermined distance, and wherein the predetermined distance is comprised between 5 and 150 microns.

2. The hook fastener according to claim 1, wherein an effective width of the overhang, measured in the lateral direction, is between 3 and 5 times the predetermined distance.

3. The hook fastener according to claim 1, wherein the minimum thickness of the overhang is equal to or greater than 0.5 times the predetermined distance, or is equal to or greater than 0.8 times said distance.

4. The hook fastener according to claim 1, wherein a maximum thickness of the overhang is at least equal to a sum of the minimum thickness and half of the predetermined distance, and is less than 5 times the predetermined distance.

5. The hook fastener according to claim 1, wherein a ratio between the hook overall height, measured from a top thereof to the base strip in the main direction of the gripping hook, and a thickness of the base strip measured in said main direction, is between 3 and 12.

6. The hook fastener according to claim 1, wherein an effective cap height, measured in the main direction of the gripping hook, from a top of the hook to a low point of the overhang, is comprised between 30 and 200 microns.

7. The hook fastener according to claim 6, wherein the-effective cap height is less than or equal to 120 microns.

8. The hook fastener according to claim 1, wherein the depth measured in the main direction of the hook, between a projection in the main direction of a reference point on the bottom surface of the overhang, and the low point of the overhang, is between 0.25 and 1 times the cavity depth.

9. The hook fastener according to claim 1, wherein a straight line connecting the low point of the overhang and a projection of a reference point, in the main direction of the hook, on the bottom surface of the overhang forms an angle comprised between 30 and 90° with a plane perpendicular to the main direction of the hook.

10. The hook fastener according to claim 1, wherein the base strip and the gripping hooks are made of a material comprising at least 70% by mass of a polyolefin or polypropylene.

11. The hook fastener according to claim 1, wherein the predetermined distance is comprised between 15 and 25 microns.

12. The hook fastener according to claim 1, wherein the bottom surface of the overhang includes a concave surface part located on the stem side and a convex surface part extending said concave surface part from an inflection point towards the distal end of the overhang.

13. The hook fastener according to claim 12, wherein the upper surface of the overhang is flat or convex at least in a region which is delimited by a first plane containing an innermost point of the stem adjacent to the overhang and a second plane containing the inflection point, said first and second planes being perpendicular to the lateral direction.

14. The hook fastener according to claim 12, wherein the minimum thickness of the overhang is measured between a first plane containing an innermost point of the stem adjacent to the overhang and a second plane containing the inflection point, said first and second planes being perpendicular to the lateral direction.

15. The hook fastener according to claim 1, wherein the cap of the gripping hook includes two overhangs which are laterally opposed.

16. The hook fastener according to claim 1, wherein a top of the gripping hook is laterally offset with respect to a central axis of the stem while remaining in an area bounded by a plane containing an innermost point of the stem adjacent the overhang and perpendicular to the lateral direction of the gripping hook.

17. The hook fastener according to claim 1, wherein a half-width of the stem, measured in the lateral direction at its narrowest portion, is comprised between 2 times the minimum thickness of the overhang and 3 times a maximum thickness of the overhang.

* * * * *